United States Patent
Naoum

(10) Patent No.: US 10,029,055 B2
(45) Date of Patent: Jul. 24, 2018

(54) NEBULIZER DEVICE AND MASK OF INHALATION SOLUTION

(71) Applicant: George Naoum, Gkizi Attikis (GR)

(72) Inventor: George Naoum, Gkizi Attikis (GR)

(*) Notice: Subject to any disclaimer, the term of this patent is extended or adjusted under 35 U.S.C. 154(b) by 7 days.

(21) Appl. No.: 14/779,297

(22) PCT Filed: Mar. 24, 2014

(86) PCT No.: PCT/GR2014/000019
§ 371 (c)(1),
(2) Date: Sep. 22, 2015

(87) PCT Pub. No.: WO2014/147430
PCT Pub. Date: Sep. 25, 2014

(65) Prior Publication Data
US 2016/0051775 A1 Feb. 25, 2016

(30) Foreign Application Priority Data
Mar. 22, 2013 (GR) ................ 20130100171

(51) Int. Cl.
*A61M 11/04* (2006.01)
*A61M 16/06* (2006.01)
(Continued)

(52) U.S. Cl.
CPC ......... *A61M 11/042* (2014.02); *A61M 11/044* (2014.02); *A61M 11/06* (2013.01);
(Continued)

(58) Field of Classification Search
CPC .. A61M 16/20; A61M 16/201; A61M 16/204; A61M 16/205; A61M 16/06;
(Continued)

(56) References Cited

U.S. PATENT DOCUMENTS 3,045,670 A    7/1962  Hirtz et al.
3,695,267 A *  10/1972 Hirtz ............... A61M 15/00
                                                   128/203.17
(Continued)

FOREIGN PATENT DOCUMENTS

AU    2002301057 B2   6/2003
EP        1369141 A1  10/2003
WO   WO2012085740 A1   6/2012

OTHER PUBLICATIONS

Notification of Transmittal of the International Preliminary Report on Patentability for International Application No. PCT/GR2014/000019 dated Jul. 16, 2015 by the EPO, Munich, Germany.
(Continued)

*Primary Examiner* — Peter S Vasat
*Assistant Examiner* — Margaret Luarca
(74) *Attorney, Agent, or Firm* — Peter B. Scull; Hamilton, DeSanctis & Cha LLP

(57) ABSTRACT

The traditions, studies and international practice, prove that the inhalation of hot steams with or without the impurity of a medicine, helps the prevention and treatment of respiratory system diseases in hospitalization or home treatment. The device of application of the therapy is simple, easy to use, safe and affordable cost. This invention concerns a system with: 1) A inventive pipe—conductor of air, with an embodied safe system of electric points and power connections—cables for the supply of the nebulizer device with air and power simultaneously. 2) A nebulizer device that permits the simultaneous heating of the solution and nebula at 35-40° C. via a temperature regulator. In addition it posses system which via the electromagnets or the mechanism opens and closes impellers or a silicone leaf and settles the provision of nebula towards the inhalation mask. 3) A mask of inhalations (Continued)

with conical channels that routes the expired air to the sensor and the inhaled nebula to the mouth and nasal cavity.

14 Claims, 6 Drawing Sheets

(51) Int. Cl.
*A61M 11/06* (2006.01)
*A61M 16/10* (2006.01)
*A61M 16/14* (2006.01)
*A61M 16/20* (2006.01)
*A61M 16/00* (2006.01)
*A61M 15/00* (2006.01)

(52) U.S. Cl.
CPC ........ *A61M 16/0003* (2014.02); *A61M 16/06* (2013.01); *A61M 16/108* (2014.02); *A61M 16/14* (2013.01); *A61M 15/0016* (2014.02); *A61M 16/20* (2013.01); *A61M 2016/0024* (2013.01); *A61M 2205/0238* (2013.01); *A61M 2205/3368* (2013.01); *A61M 2205/3653* (2013.01)

(58) Field of Classification Search
CPC .............. A61M 16/0003; A61M 16/14; A61M 16/108; A61M 16/0016; A61M 11/042; A61M 11/06; A61M 11/044; A61H 33/12
USPC .......................... 128/200.14, 203.16, 203.17
See application file for complete search history.

(56) References Cited

U.S. PATENT DOCUMENTS

| 4,190,046 | A | 2/1980 | Virag |
| 4,195,044 | A | 3/1980 | Miller |
| 4,566,450 | A | 1/1986 | Brossman, Jr. |
| 4,635,630 | A | 1/1987 | Noir et al. |
| 4,819,625 | A * | 4/1989 | Howe .................. A61M 16/16 128/200.14 |
| 4,911,157 | A | 3/1990 | Miller |
| 5,259,370 | A | 11/1993 | Howe |
| 5,727,542 | A | 3/1998 | King |
| 6,983,923 | B2 | 1/2006 | Fukui et al. |
| 7,396,995 | B2 | 7/2008 | Laurent et al. |
| 2003/0120157 | A1 | 6/2003 | Fukui et al. |
| 2004/0182855 | A1* | 9/2004 | Centanni .................. A61L 2/07 219/628 |
| 2005/0229929 | A1* | 10/2005 | Ivri ...................... A61M 11/005 128/203.12 |
| 2006/0003030 | A1* | 1/2006 | Chun-Ying .......... A61K 36/237 424/725 |
| 2007/0079982 | A1* | 4/2007 | Laurent ................ A61M 16/08 174/68.1 |
| 2008/0142010 | A1 | 6/2008 | Weaver et al. |
| 2008/0271732 | A1 | 11/2008 | Weaver |
| 2009/0312661 | A1* | 12/2009 | Kullik ................. A61B 5/0876 600/538 |
| 2012/0186582 | A1* | 7/2012 | Addington ............ A61M 11/06 128/200.21 |
| 2013/0172772 | A1* | 7/2013 | Alshaer ................. A61B 5/087 600/538 |

OTHER PUBLICATIONS

International Search Report for PCT Application No. PCT/GR2014/000019 issued by the European Patent Office, dated Jul. 30, 2014, 5 pages, Rijswijk, NL.

Warren Finlay, Sub-Chapter 8.13, Nebulizer efficiency and output rate of/from Chapter 8, Jet Nebulizers, The Mechanics of Inhaled Pharmaceutical Aerosols, Jun. 19, 2001, excerpt p. 216 for sub-Chap 8.13, provided, from chap. 8, First Edition, Academic Press, Science Direct, Elsevier Ltd., Amsterdam, NL.

* cited by examiner

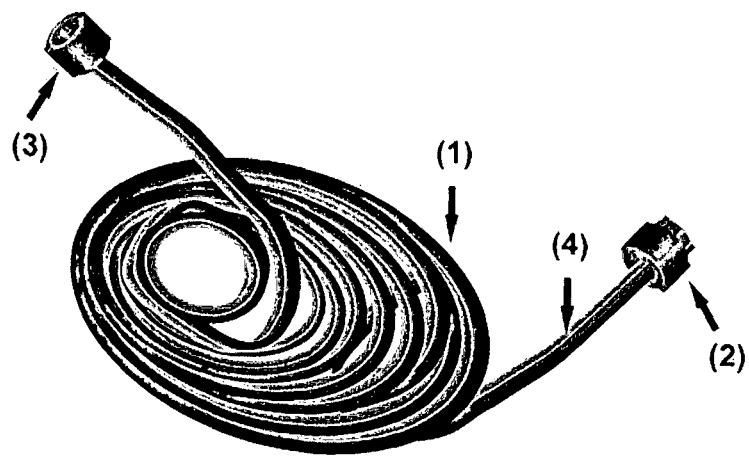
DRAWING 1
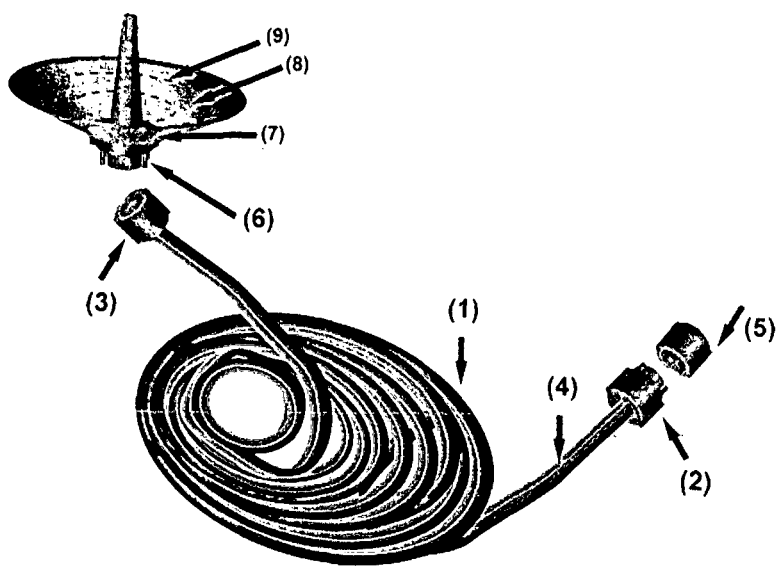
DRAWING 2

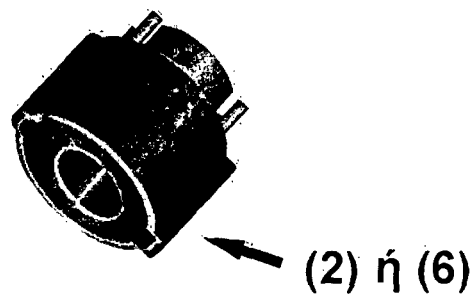
DRAWING 3
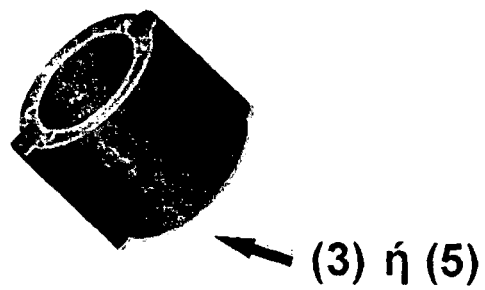
DRAWING 4

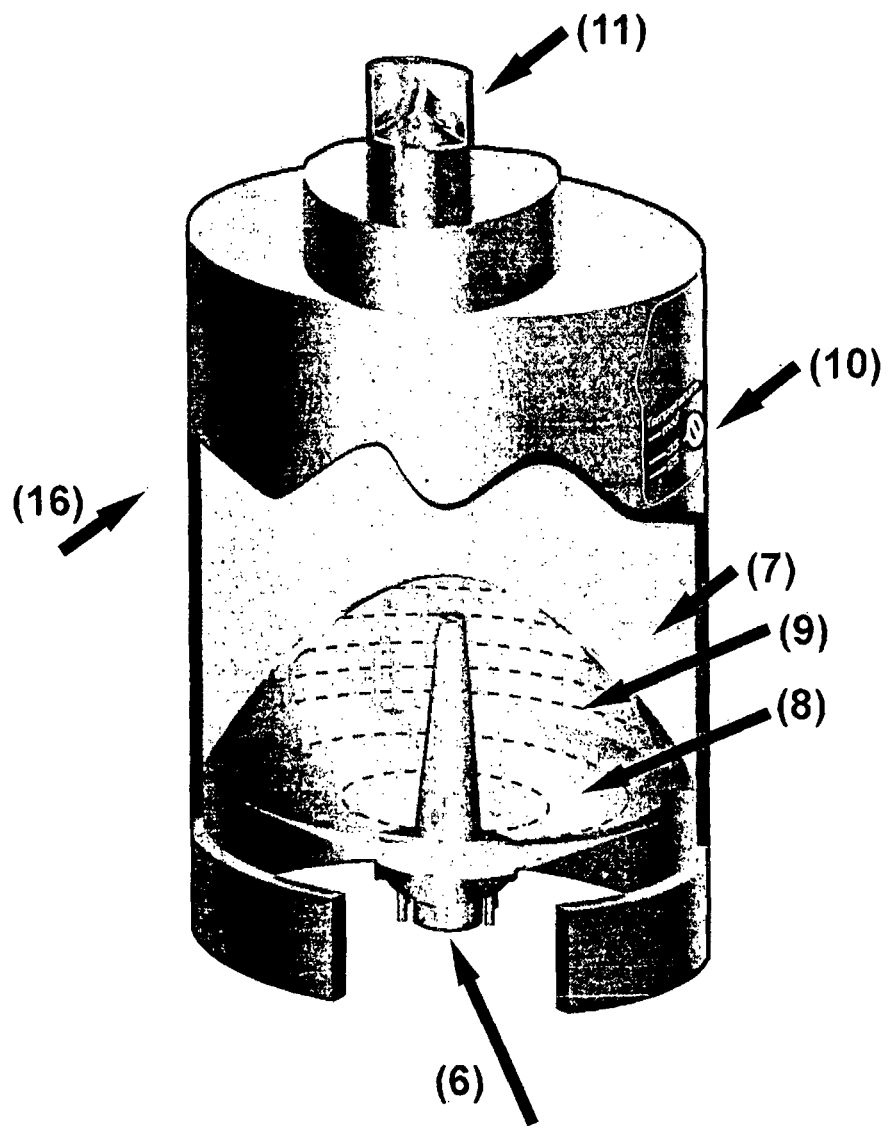
DRAWING 5

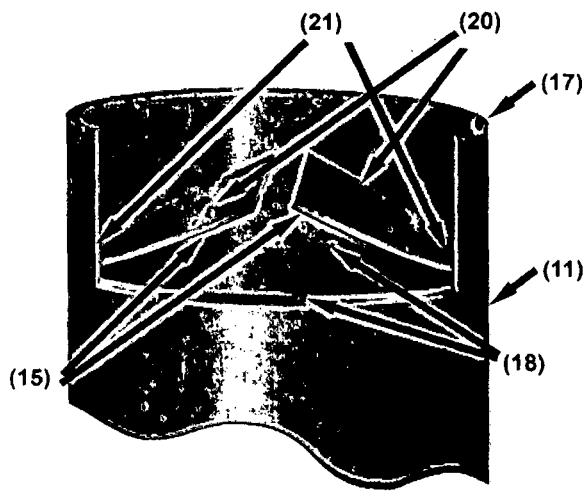
DRAWING 6
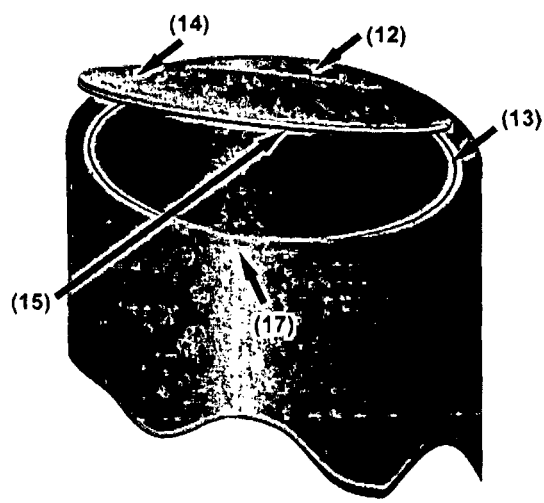
DRAWING 7

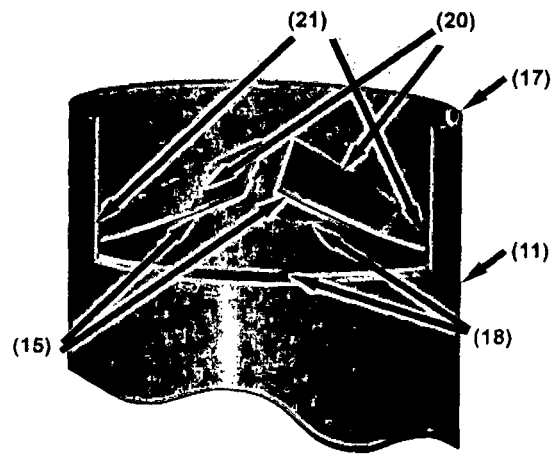
DRAWING 8
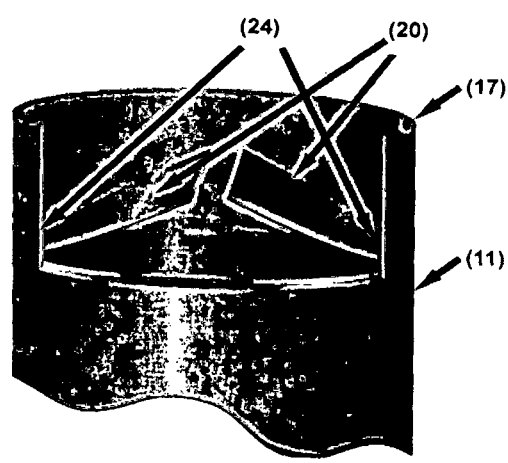
DRAWING 9

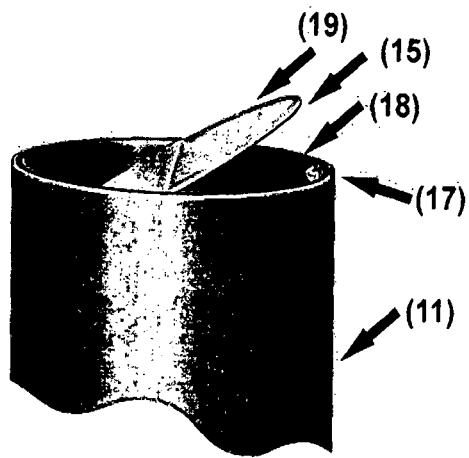
DRAWING 10
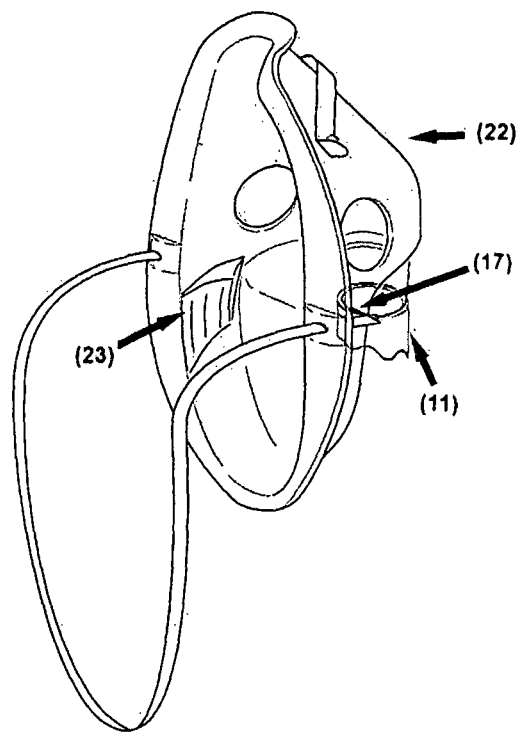
DRAWING 11

NEBULIZER DEVICE AND MASK OF INHALATION SOLUTION

The invention relates to a system of hot-nebulized solution provision, consisted of an air pipe—duct with embodied system of connectors—power connections—cables, in a device of nebulizer, for the controlled provision of heated nebulized pharmaceutical solution or hot nebulized solution containing essential oils and decoctions' distillates or simple hot nebula for inhalation, and a mask for the therapy or prevention of diseases of the respiratory system. Its use is suggested either for hospital use connected with the central oxygen provider or for therapy at home connected with a device providing compressed air.

There are many types of devices and masks providing inhaled pharmaceutical solutions either in hospitalization or at home nursing. In the first case the devices function by their connection with the central oxygen provider and in the second ease with the connection with a portable a device providing compressed air.

In both practices the temperature of the pharmaceutical solution or the normal saline with any additions is low, about 10 Celsius degrees and does not have the therapeutic advantage of hot steam, which is a very important disadvantage in the everyday medical practice.

The present application has important advantages against the already existing devices, and for their understanding the reference in some parameters is required.

From the traditions of most of the people we know that in order to assist the organism to confront infections and disorders of the respiratory system, is proposed besides everything else, the consumption of hot decoctions or drinks and the use of humidifiers in the rooms (mainly in children's rooms).

This is justified because the people and the scientific medical knowledge of fluctuant level, through the crossing of centuries, noticed that various drinks and hot water vapors offer warmth in the mucosa and accelerate the therapy. By humidifying with hot steam the mucosa of the bronchial tree, the excreta are liquefied and discharged easier, the surface of the mucosa is cleaned and so is succeeded the action of the pharmaceutical substance transferred by the steam and the warmth of hot steam and medicinal characteristics of the decoctions in the cells of the mucosa of the bronchial tree.

This is also supported by modern medical practice worldwide. In addition, today science knows that hot steam, especially hot nebulized solutions act profitably in human organism.

The benefits from the inhalation of hot nebulized solutions in mild infections of the respiratory system are pointed out in the internet, for example at the NHS for the public (NHS choices), as well as in heavy infections of the respiratory system as mentioned in the international literature, by the use of moisture and heat of the inhaled gas in body temperature in Intensive Care Unit conditions (Crit Care Med 1996; 24:1920-1929).

This brief description of the benefits of inhaled hot steam in the bronchial tree, 2, 06 leads to the view that it is more profitable to add the affection of heat, in various therapies with inhaled bronchodilators, anti-inflammatory and antibiotics applied till today in every day medical practice.

By the nebulizers known today, the temperature of the inhaled final product varies between 10 to 15° C., respectively to the volume and the speed of the flow of the air provided by the devices. The cold nebulized solution with or without added medicines, reaches the mucosa of the respiratory system that has temperature of 37° C. up to 40° C. in infections.

Despite the heat that gets by the air ducts of the upper respiratory system (cavity of the mouth, oral part of pharynx, larynx), the temperature of the nebula that reaches the lower respiratory system is much lower than the temperature of the mucosa, and that does not offer the required warmth in the respiratory system.

In addition by the gases kinetics we know that, the duplication of the temperature increases the speed of masses of gasses per 1.41 times in stable conditions of pressure, volume and composition.

That means that the nebulized solution of the medicinal substance of 40° C. will have a transfer speed 1.41 times greater than the speed of the steam of 20° C. serum.

Keeping in view that by the nebulizers being used the temperature of the inhaled final nebula varies between 10 to 15° C. is concluded that the speed of transfer of the spay of 35 to 40° C. will be almost triple.

By all odds in this case by inhalation the spray will reach in a larger depth in network of air ducts of the lung and therefore the therapeutic result will be better and the cure will be quicker.

The serum constitutes the excipient of the added chemical substance of the bronchodilators or anti-inflammatory medicines or antibiotics or oils, which by its spinning in the device is nebulized-The nebulized solution in 40° C. has lower density per cc and more than double speed of transfer from the one in 20° C. These characteristic of the hot nebula, enables it to be easier inhaled and as a result to enter in a greater depth of the bronchial tree in the unit of the time and with a deeper inhalation to reach up to the level of small air ducts.

It is obvious that in case of inhalation of hot nebulas of the therapeutic substance, the therapeutic result will be better. In addition we will have the profitable effect of the heat in the anaplasis of the sick mucosa of the bronchial tree and the best liquidation and absorption of excretions.

For the above mentioned reasons we have a greater bronchodilitation, assistance, the therapy of mucosa, the facilitation of abortion of the excretions via the expectoration, the amelioration of the respiratory ability of the patient, and its quicker.

The same happens in home nursing too, by the use of the nebulizer.

Beside the therapy of the diseases of the respiratory system important value has the preventive cleaning of the respiratory system.

The inhaled air of the encumbered environment of the modern society, mainly of the large urban centers, causes permanent troubles in the normal function of the mucosa of the respiratory system.

The respiratory system of smokers and employees in close work areas with technical heat—freezing, half-freshened air and industries, mines etc, is aggravated more.

Creeping small infections, increase of the production of high viscosity excretions, difficulty in hawking and cleaning of the bronchial tree, constitute some of the encumbrances of the respiratory operation. The common and most of times permanent aggravated of the operation of the respiratory system increases the possibility of pathologic troubles of the respiratory system such as chronic bronchitis, bronchial asthma, COPD (chronic obstructive pulmonary disease, emphysema, lung cancer etc.

The application with the device of frequent cleanings of the respiratory system, with weekly doses of inhalations of heat nebula and the addition of essential oils of eucalyptus or decoctions, constitutes a choice of preventive therapy of the respiratory system in order to preserve the organism from pathologic troubles and to guaranty to human being a better quality of life.

In addition is known that by the total of the provided therapeutic substance through inhaled medicines, only 10% approximately reaches the pneumonic parenchyma which is the target for treatment.

It happens because we have losses during inhalation and expiration, as follows:

During expiration the produced spray is not inhaled, as it is logic, neither is aborted in the environment, so we have an important loss.

During inhalation and respectively to the inhaling ability of each patient, 10% to 30% of the produced spray is not inhaled.

The particles of the pharmaceutical substance of 2-5 microns are subject to precipitation and infraction in the mucosa of air ducts of the respiratory system, whereas the particles being smaller than 2 microns are expired.

30% to 60% of the medicine lays down in the oral part of the pharynx during the inhalation.

Approximately 10% stay in the walls of the device.

Considering the scientific marking we proceed to the study and development of a nebulizer device and an inhalation mask with an embodied system for simultaneous heating of the normal saline or the normal saline mixed with essential oils or the pharmaceutical solution and of the produced nebula, with temperature regulator of 35-40° C. which is pleasurably affordable by the patient, easy to use and absolutely safe.

This device consists of
1) The air—power pipe-conductor
2) The device of nebulization of the serum (nebulizer) and
3) The inhalation mask
More specifically:
Air—Power Pipe—Conductor:

In the two ends of the pipe—conductor (1) there are embodied, a thin safety power connection (2) in the central end and a safety electric point (3) in the peripheral end, being connected with thin cables (4) across the body of the treatment pipe. The central end ends at the provision of the air volume, which provision bears a thin safety electric point (5). The same stands, on the opposite direction in the peripheral end where the electric point (3) of the treatment pipe provides power to the power connection (6) located in the base of the nebulization device (16), peripherically to the reception mouth of the treatment pipe. By this construction we simultaneously have provision of air and power without complicating or obstructing the common movement of connection of the air duct with the provision, as it is currently applied worldwide.

Device of Nebulization of the Serum (Nebulizer):

The nebulizer (16) is consisted of the main body of spraying (7) with conical cuplike internal base. The interior of the device is coated with a thin and slim leaf of refractory material (8) that embodies a rich network of heat resistances (9) in its whole internal surface connected with the power connection (6). The coating heats simultaneously the included serum or solution and the produced for inhalation nebula, in the regulated by the regulator (10) temperature up to 40° C.

The upper outlet of the spray (11) is round, and in the back side it bears a conical flat area (12). In the anterior edge of the mouth there is an electronic sensor (17), sensitive in the fluctuation of the pressure of the air by the expiration of the patient. By this stimulant of the patient has the ability to change the polarity of a semi-circular electromagnet (13) in the surface of the edge of the mouth or electromagnets (18), located in the internal surface of the spray exit mouth. In the surface of the flat area is based a circular silicone leaf (14) of diameter equal to the mouth, which moves upwards and downwards, closes or opens the equal in size mouth of the nebula's exit, excludes or permits respectively the exit of the air to the mask of inhalation and brings to periphery magnet poles (15) of opposite polarity (heteronyms) with the electromagnet (13) of the mouth of the edge of the exit that results to the closing of the mouth. In the other version the sensor (17) changes the polarity of the electromagnets (18) and by a proportional way (homonyms to heteronyms charges): a) moves around its axis by vertical to horizontal position and vice versa, a round impeller (19), of equal diameter with the nozzle of the mouth that in periphery has a couple of magnets (20) or b) two wings of semi-circular shape move, of total diameter equal to the cross-section of the mouth, based on the walls of the nozzle (22), move from horizontal position to vertical and vice versa and obstacle or permit the passage of the spray. In the end of each expiration and before the beginning of the inhalation, the sensor (17) changes the polarity of the magnets (13) or (18) and the leaf of silicone or the impellers (19) or (21) close the mouth (11), and obstacle the exit of the steam in order to save the pharmaceutical substance, which by the devices being used is lost in the environment. In addition, whereas the mouth is close, inside the device the pressure of the steam is increased and therefore in the phase of inhalation, the steam is ejected with greater pressure, density and temperature towards the mouth and the nose of the patient, with obvious better results.

By another version, the sensor (17) activates a thin mechanical system consisted of springs found at the same place (13) or (18) and the specific system has exactly the same valvular operation with electromagnets.

Inhalation Mask:

An inhalation mask with the suitable constructions of conical channels (23) at the internal side, routes the expired air towards the mouth of exit of the nebula, where the sensor is found and vice versa during inhalation, the nebula to the mouth and nasal cavity.

This invention differs and excels from other inventions having the same purpose, namely the provisions of heat solutions for inhalation. For example, in comparison with the U.S. Pat. No. 4,911,157/27 Mar. 1990 or the US2008142010, or U.S. Pat. No. 3,045,670 the present application differs among others in the following:

1) it has an embodied to the air pipe—air-duct system, an electric point 2) simultaneously heats the solution and the nebula at the temperature of choice 3) has a system of periodic interruption and provision of spray during expiration and inhalation respectively.

4) Is a simple device, easy to use, safe, light and effective 5) the required actions for its installation are very simple in comparison with the common nebulizer devices.

6) it is a nebulizer, not humidifier and it produces nebula of droplets of liquid and pharmaceutical substance from the high pressure gas according to the Bernulli law.

7) the interior of the whole device is coated with a refractory material

8)) it comprises a rich network of heat resistances (9) in its whole internal surface with which it heats simultaneously the solution and the produced nebula, so that temperature of choice is always the same for the nebula until the inhalation outlet For the above mentioned reasons the present application is new, inventive and has industrial application The drawings that follow describe the device for the best understanding of the reader:

Drawing 1: The air-power pipe—conductor with the two (2) edges, central and peripheral Drawing 2: The air-power pipe—conductor with the corresponding connections of the edges with the electric point (central power and air provision) and power connection (nebulizer device)

Drawing 3 and 4: Description of the electric points and power connections Drawing 5: The nebulizer device Drawing 6, 7, 8, 9, 10: The alternative systems (valves) for the controlled provision of spray Drawing 11: Inhalation Mask

The invention claimed is:

1. A nebulizer device, connectable to an inhalation mask, the nebulizer device comprising:
    a main body, including:
        a liquid solution;
        an interior surface, coated with a coating of refractory material the entire coating incorporating a network of heat resistors on the whole interior surface of the main body;
        a reception mouth, connectable to an air-power pipe conductor, to receive compressed air and power from the air-power pipe conductor to supply power to the heat resistors and supply compressed air to the interior of the main body to produce a produced spray nebula by the Bernoulli principle from the included liquid solution disposed within the main body, the main body and reception mouth being configured for the compressed air flow under the Bernoulli principle to create a relative low pressure adjacent the included liquid solution in the main body for the included liquid solution to form nebula droplets suspended in air to form the produced spray nebula;
        an outlet to provide the produced spray nebula to the inhalation mask;
        a system of periodic interruption and provision of the spray nebula during exhalation and inhalation, respectively,
    the network of heat resistors on the whole interior surface being configured to heat the liquid solution and the produced spray nebula and maintain the temperature of the liquid solution and the produced spray nebula within an operative range during nebulization and until the spray nebula reaches the outlet to the inhalation mask.

2. The nebulizer device according to claim 1, further comprising an air-power pipe conductor, the air-power pipe conductor having a body and two ends, one end of the two ends comprising an electrical power connection and the other end of the two ends comprising another electrical power connection, said two ends being connected with thin cables along the body of the air-power pipe conductor, the one end being connectable to a compressed air volume supply, the compressed air volume supply bearing a further electrical power connection; the electrical power connection of the air power pipe conductor being configured to provide power to a power connection located at the reception mouth located at a base of the interior, peripherally to the reception mouth.

3. The nebulizer device according to claim 2:
    the base being a conical cuplike internal base, said heat resistors being connected to the power connection of the reception mouth, and,
    the nebulizer device further comprising a temperature regulator to regulate the temperature of the liquid solution and the spray nebula between 35° C.-40° C.;
    the outlet being round and bearing at a back side thereof a conical area of diameter equal to the outlet mouth's diameter;
    and the nebulizer further comprising semi-circular electromagnets disposed in a surface of an internal edge of the mouth of the outlet;
    the system of periodic interruption and provision of the spray nebula during expiration and inhalation comprising:
    an electronic sensor, in an anterior edge of the mouth of the outlet, sensitive to the fluctuation of the pressure of the air by the expiration of the patient, and
    a circular silicone leaf of diameter equal to the mouth's diameter and disposed based in a surface of the conical area, said circular silicone leaf being moveable upwards and downwards
    the silicone leaf having in its periphery magnetic poles;
    the sensor being configured to change the polarity of the electromagnets to move the silicone leaf and close the outlet when the patient expires.

4. The nebulizer device according to claim 2:
    the base being a conical cuplike internal base, said heat resistors being connected to the power connection of the reception mouth, and,
    the nebulizer device further comprising a temperature regulator to regulate the temperature of the liquid solution and the spray nebula between 35° C.-40° C.;
    the outlet being round and bearing at a back side thereof a conical area of diameter equal to the outlet mouth's diameter and being configured to open or close;
    and the nebulizer further comprising semi-circular electromagnets disposed in a surface of an internal edge of the mouth of the outlet;
    the system of periodic interruption and provision of the spray nebula during expiration and inhalation comprising:
    an electronic sensor, in an anterior edge of the mouth of the outlet, sensitive in the fluctuation of the pressure of the air by the expiration of the patient, and
    a round impeller of diameter equal to the diameter of the mouth having a pair of magnets at its periphery, the round impeller being configured to move from vertical to horizontal position and vice versa and
    the sensor being configured to change the polarity of the electromagnets to be of opposite polarity to the polarity of the pair of magnets when the patient expires to move the round impeller from vertical to horizontal position to close the outlet.

5. The nebulizer device according to claim 2:
    the base being a conical cuplike internal base, said heat resistors being connected to the power connection of the reception mouth, and,
    the nebulizer device further comprising a temperature regulator to regulate the temperature of the liquid solution and the spray nebula between 35° C.-40° C.;

the outlet being round and bearing at a back side thereof a conical area of diameter equal to the outlet mouth's diameter and being configured to open or close;

and the nebulizer further comprising semi-circular electromagnets disposed in a surface of an internal edge of the mouth of the outlet;

the system of periodic interruption and provision of the spray nebula during expiration and inhalation comprising:

an electronic sensor, in an anterior edge of the mouth of the outlet, sensitive in the fluctuation of the pressure of the air by the expiration of the patient, and two wings of semi-circular shape disposed on walls of the mouth of the opening and of total diameter equal to the cross-section of the mouth of the outlet, and configured to move from horizontal position to vertical and vice versa, the sensor being configured to change the polarity of the electromagnets to move the wings from horizontal position to vertical and vice versa to stop or permit the passage of the spray nebula, respectively.

6. The nebulizer device according to claim 2, further comprising:

a thin mechanical system comprising thin springs, the thin mechanical system being disposed at a surface of an internal edge of the opening;

a back side bearing a conical area of diameter equal to the mouth's diameter, coupled to the opening; and, an electronic sensor disposed in an anterior edge of the outlet, the nebulizer device providing periodic interruption and provision of the spray nebula during exhalation and inhalation, respectively.

7. The nebulizer device according to claim 3, further comprising an inhalation mask, the inhalation mask having constructions of conical channels at the internal side configured to route the expired air towards the mouth of the opening, where the electronic sensor is disposed, and to route the spray nebula to the mouth and nasal cavity of the patient.

8. The nebulizer device according to claim 1, the liquid solution being saline.

9. The nebulizer device according to claim 1, the liquid solution being saline mixed with essential oils.

10. The nebulizer device according to claim 1, the liquid solution being saline mixed with decoctions' distillates.

11. The nebulizer device according to claim 1, the liquid solution including a pharmaceutical substance.

12. The nebulizer device according to claim 4, further comprising an inhalation mask, the inhalation mask having constructions of conical channels at the internal side configured to route the expired air towards the mouth of the opening, where the electronic sensor is disposed, and to route the spray nebula to the mouth and nasal cavity of the patient.

13. The nebulizer device according to claim 5, further comprising an inhalation mask, the inhalation mask having constructions of conical channels at the internal side configured to route the expired air towards the mouth of the opening, where the electronic sensor is disposed, and to route the spray nebula to the mouth and nasal cavity of the patient.

14. The nebulizer device according to claim 6, further comprising an inhalation mask, the inhalation mask having constructions of conical channels at the internal side configured to route the expired air towards the mouth of the opening, where the electronic sensor is disposed, and to route the spray nebula to the mouth and nasal cavity of the patient.

* * * * *